United States Patent [19]

Atwater et al.

[11] Patent Number: 5,280,548
[45] Date of Patent: Jan. 18, 1994

[54] EMISSION BASED FIBER OPTIC SENSORS FOR PH AND CARBON DIOXIDE ANALYSIS

[75] Inventors: Beauford W. Atwater, Bernardsville; Olga Laksin, Scotch Plains, both of N.J.

[73] Assignee: BOC Health Care, Inc., Liberty Corner, N.J.

[21] Appl. No.: 3,090

[22] Filed: Mar. 11, 1993

[51] Int. Cl.⁵ .............................................. G02B 6/00
[52] U.S. Cl. ........................................ 385/12; 385/143
[58] Field of Search ................................... 385/12, 143

[56] References Cited

U.S. PATENT DOCUMENTS 5,127,730 7/1992 Brelje et al. ........................ 356/318
5,196,709 3/1993 Berndt et al. ..................... 250/458.1

Primary Examiner—Frank Gonzalez
Assistant Examiner—Stephen W. Barns
Attorney, Agent, or Firm—R. Hain Swope; Larry R. Cassett

[57] ABSTRACT

The present invention is directed to a fiber optic sensor for analyzing pH which comprises (a) a fluorescence-based fiber optic sensor; and (b) a fluorescent dye-polymeric matrix in contact with the sensor, wherein the fluorescent dye is seminaphthorhodaflor-1-isothiocyanate, the polymer is a hydrogel selected from the group consisting of polyhydroxyethylmethacrylate, polyvinylpyrrolidone, cellulose, dextrans, and polysaccharides, and the dye is chemically bonded to the polymer. The present invention is also directed to a fiber optic sensor for analyzing carbon dioxide which comprises (a) a fluorescence-based fiber optic sensor; and (b) a fluorescent dye-polymeric-silicone elastomeric matrix in contact with the sensor, wherein the matrix comprises a fluorescent dye-polymeric premixture in a silicone elastomer, and the fluorescent dye is selected from the group consisting of seminaphthorhodaflor-1-carboxylate (SNARF-1C), seminaphthorhodaflor-1-isothiocyanate (SNARF-1C-ITC), seminaphthorhodaflor-1-dextran conjugate (SNARF-1C-Dex), 10-diethylamino seminaphthorhodaflor-1-carboxylate (SNARF-2C), and seminaphthorhodaflor-1-carboxylate 10-acetate (SNAFL-1C diacetate), the polymer is a hydrogel selected from the group consisting of polyhydroxyethylmethacrylate, polyvinylpyrrolidone, cellulose, dextrans, and polysaccharides, and the silicone elastomer is a polydimethyl siloxane selected from the group consisting of hydroxy, epoxy, and vinyl terminated polydimethyl siloxanes.

19 Claims, 9 Drawing Sheets

SNARF-1C, R=CH₃
SNARF-2C, R=CH₂CH₃

SNARF-1C-ITC

SNAFL-1C DIACETATE

FIG.2
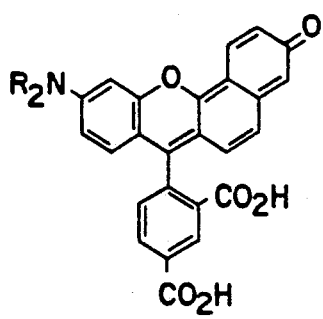
SNARF-1C, R=CH3
SNARF-2C, R=CH2CH3
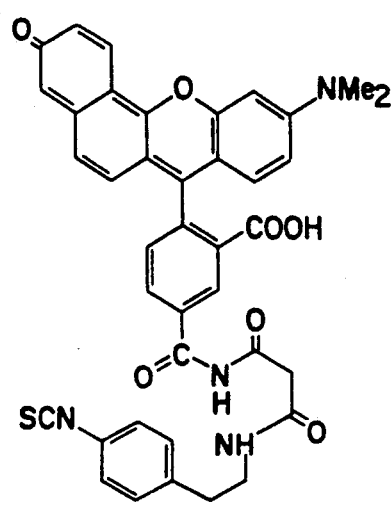
SNARF-1C-ITC
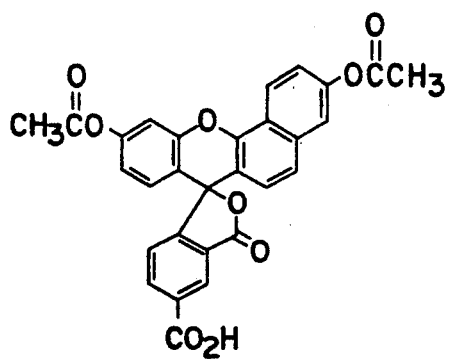
SNAFL-1C DIACETATE

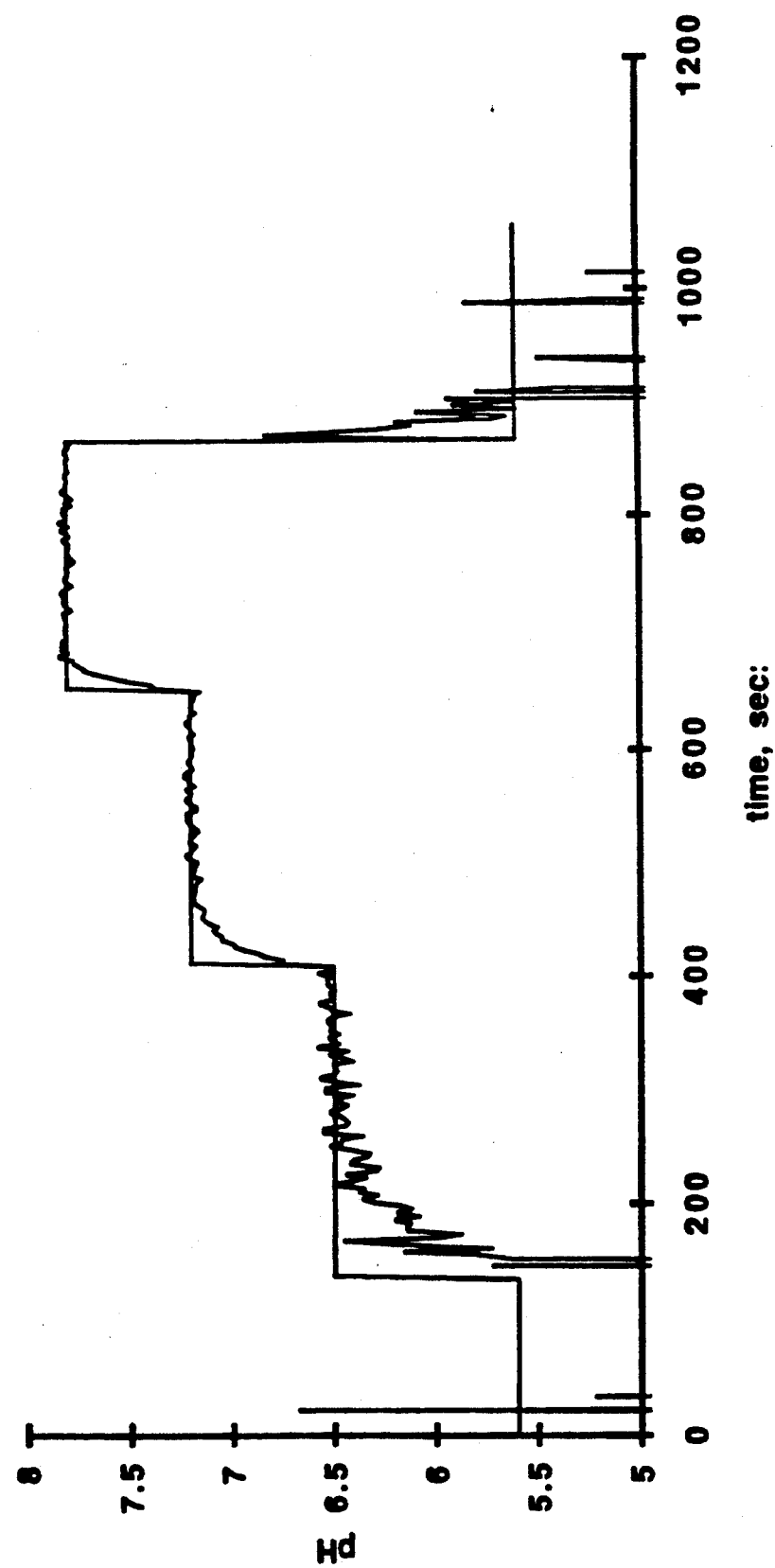

EMISSION BASED FIBER OPTIC SENSORS FOR PH AND CARBON DIOXIDE ANALYSIS

FIELD OF THE INVENTION

The present invention is directed to fiber optic sensors for the analysis of pH and carbon dioxide in liquids. In one embodiment, the invention is directed to a pH fiber optic sensor which comprises a fiber optic sensor coated with a pH sensitive fluorescent dye-polymeric matrix. In another embodiment, the invention is directed to a carbon dioxide fiber optic sensor which comprises a fiber optic sensor coated with a carbon dioxide sensitive fluorescent dye-polymeric-silicone elastomeric matrix.

BACKGROUND OF THE INVENTION

Optical pH and carbon dioxide sensors are an active area of research [Leiner, Marc J. P., Wolfbeis, Otto S. In *Fiber Optic Chemical Sensors*, Wolfbeis, Otto S., Ed., Chapter 8, CRC Press: Boca Raton, 1991]. Recently, several pH sensitive seminaphthorhodaflor dyes have been reported which can be excited in the green part of the spectrum and have emission from both the acid and base tautomers [Whitaker, James E., Haugland, Richard P., Prendergast, Franklyn G. Anal. Biochem., 1991, 194, 330–44]. Fiber optic sensors fabricated with these seminaphthorhodaflor dyes have many advantages over conventional sensors. For example, such sensors may use inexpensive green light emitting diodes and the ratio between the emission from the base peak and the isosbestic point, in contrast to the emission from the base peak alone, is impervious to many effects associated with luminescence-based optic fiber sensors such as bending loss, connector loss, photobleaching, etc. Consequently, fiber optic sensors fabricated with seminaphthorhodaflor dyes inherently have much lower drift than current fluorescent sensors.

SUMMARY OF THE INVENTION

In one embodiment, the present invention is directed to a fiber optic sensor for analyzing pH which comprises (a) a fluorescence-based fiber optic sensor; and (b) a fluorescent dye-polymeric matrix in contact with the sensor, wherein the fluorescent dye is seminaphthorhodaflor-1-isothiocyanate, the polymer is a hydrogel selected from the group consisting of polyhydroxyethylmethacrylate, polyvinylpyrrolidone, cellulose, dextrans, and polysaccharides, and the dye is chemically bonded to the polymer.

In another embodiment, the present invention is directed to a fiber optic sensor for analyzing carbon dioxide which comprises (a) a fluorescence-based fiber optic sensor; and (b) a fluorescent dye-polymeric-silicone elastomeric matrix in contact with the sensor, wherein the matrix comprises a fluorescent dye-polymeric premixture in a silicone elastomer, and the fluorescent dye is selected from the group consisting of seminaphthorhodaflor-1-carboxylate (SNARF-1C), seminaphthorhodaflor-1-isothiocyanate (SNARF-1C-ITC), seminaphthorhodaflor-1-dextran conjugate (SNARF-1C-Dex), 10-diethylamino seminaphthorhodaflor-1-carboxylate (SNARF-2C), and seminaphthorhodaflor-1-carboxylate 10-acetate (SNAFL-1C diacetate), the polymer is a hydrogel selected from the group consisting of polyhydroxyethylmethacrylate, polyvinylpyrrolidone, cellulose, dextrans, and polysaccharides, and the silicone elastomer is a polydimethyl siloxane selected from the group consisting of hydroxy, epoxy, and vinyl terminated polydimethyl siloxanes.

BRIEF DESCRIPTION OF THE FIGURES

FIG. 2 illustrates the chemical structures of the fluorescent dyes ' seminaphthorhodaflor-1-carboxylate (SNARF-1C) and seminaphthorhodaflor-1-carboxylate isothiocyanate (SNARF-1C-ITC). FIG. 2 also illustrates the chemical structures of the analogs 10-diethylamino seminaphthorhodaflor-1-carboxylate (SNARF-2C) and seminaphthorhodaflor-1-carboxylate 10-acetate (SNAFL-1C diacetate).

FIG. 5B is a graph illustrating the performance of a pH fiber optic sensor plotted as a function of time in a 6.5, 7.2, and 7.8 pH buffer solution coated on 125$\mu$ optic fibers.

DETAILED DESCRIPTION OF THE INVENTION

Figure 1:
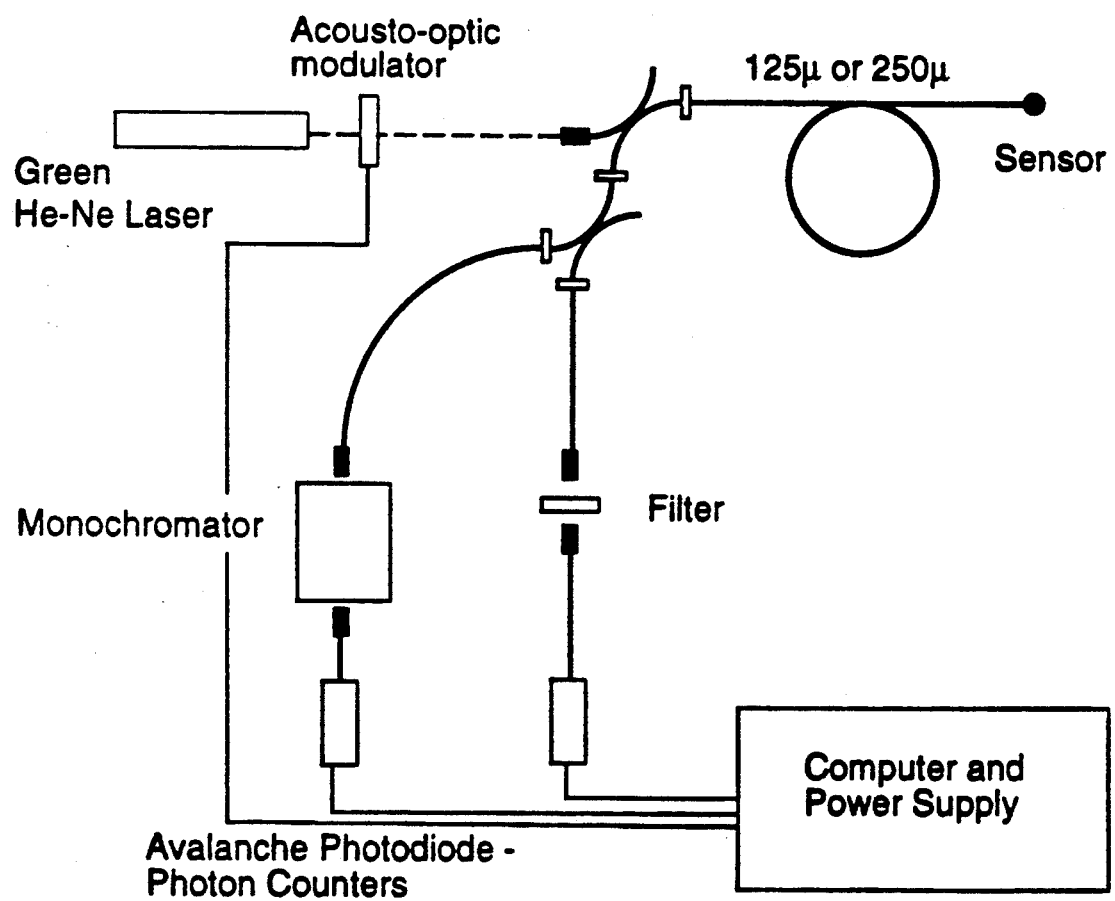
FIG. 1 is a schematic diagram of the fluorometer instrumentation used to evaluate the pH and carbon dioxide fiber optic sensors of the present invention.

The present invention is directed to fiber optic sensors for analyzing pH and carbon dioxide in liquids. The sensors measure the fluorescent emission of a dye capable of sensing changes in pH. In one embodiment, the invention is directed to a pH fiber optic sensor which comprises a fiber optic sensor coated on the distal end with a pH sensitive fluorescent dye-polymeric matrix. The fluorescent dye-polymeric matrix in the pH sensor comprises a seminaphthorhodaflor-1-isothiocyanate dye chemically bonded to the polymer to prevent the dye from being leached away from the sensor. In another embodiment, the invention is directed to a carbon dioxide fiber optic sensor which comprises a fiber optic sensor coated on the distal end with a carbon dioxide sensitive fluorescent dye-polymeric-silicone elastomeric matrix. The fluorescent dye-polymeric-silicone elastomeric matrix in the carbon dioxide sensor comprises a fluorescent dye-polymeric premix in a carbon dioxide permeable silicone elastomer. The fluorescent dye need not be chemically bonded to the polymer in the carbon dioxide sensor because the silicone elastomer also serves to entrap the dye on the sensor. The sensors perform over the ranges of physiological interest (pH 6.8–7.8 and $PCO_2$ 10–100 mm(Hg)). Two wavelengths of the emission spectrum from the dye may be mathematically combined to eliminate drift and facilitate calibration of the sensor. The sensor performance is unaffected by ambient light and photobleaching. The fiber optic sensors of the present invention may be employed in the chemical, industrial, environmental, and biomedical areas. The fiber optic sensors are useful for remote analysis because they are small, flexible, and easy to handle, and are especially useful for in vivo measurements in blood and in tissue.

As set out above, the fiber optic sensors of the present invention comprise a fiber optic sensor, a fluorescent dye, a polymeric hydrogel and, in the case of a carbon dioxide fiber optic sensor, a carbon dioxide permeable silicone elastomer. The fiber optic sensors in the present invention are fluorescence-based sensors. Fluorescence-based fiber optic sensors are preferred over absorption-based sensors and colorimetric fiber sensors because the pH and carbon dioxide sensitive dye-polymeric matrix can be applied directly to the distal end of a luminescence-based fiber without applying reflective surfaces [Bacci, M., Baldini, F., Cosi, F., Conforti, G., Scheggi, A. M. Proc. OFS'89, 6th Intern. Conf. "Optical fiber sensors", 1989, 425–430].

The pH and carbon dioxide sensitive dyes employed in the sensors are fluorescent dyes which can be excited in the green part of the spectrum and which have emission from both acid and base tautomers. In the pH fiber optic sensors, the pH sensitive fluorescent dye is chemically bonded to the polymer and is preferably seminaphthorhodaflor-1-carboxylate isothiocyanate (SNARF-1C isothiocyanate, SNARF-1C-ITC). In the carbon dioxide fiber optic sensors, the carbon dioxide sensitive fluorescent dyes need only be mixed with the polymer and may be seminaphthorhodaflor dyes selected from the group consisting of seminaphthorhodaflor-1-carboxylate (SNARF-1 carboxylate, SNARF-1C), seminaphthorhodaflor-1-carboxylate isothiocyanate (SNARF-1C isothiocyanate, SNARF-1C-ITC), and seminaphthorhodaflor-1-carboxylate dextran conjugate (SNARF-1C dextran conjugate, SNARF-1C-Dex). The seminaphthorhodaflor dyes may also be selected from the group consisting of 10-diethylamino seminaphthorhodaflor-1-carboxylate (SNARF-2C) and seminaphthorhodaflor-1-carboxylate 10-acetate (SNAFL-1C diacetate) (see FIG. 2). Preferably, the seminaphthorhodaflor dye in the carbon dioxide sensor is selected from the group consisting of seminaphthorhodaflor-1-carboxylate, seminaphthorhodaflor-1-isothiocyanate, and seminaphthorhodaflor-1-dextran conjugate. More preferably, the seminaphthorhodaflor dye in the carbon dioxide sensor is seminaphthorhodaflor-1-carboxylate.

The polymers used to support the fluorescent dyes in the pH and carbon dioxide fiber optic sensors are polymers having physical properties similar to that of living tissue and which are easy to process. The polymers may be hydrogels selected from the group consisting of polyhydroxyethylmethacrylate, polyvinylpyrrolidone, cellulose, dextrans, and polysaccharides. Preferably, the hydrogel polymer is selected from the group consisting of polyhydroxyethylmethacrylate, polyvinylpyrrolidone, cellulose, and dextrans. More preferably, the hydrogel polymer is selected from the group consisting of polyhydroxyethylmethacrylate and polyvinylpyrrolidone. Most preferably, the polymer is polyhydroxyethylmethacrylate which has physical properties similar to that of living tissue [Brannon-Peppas, L., Peppas, N. A. Biomaterials 1990, 11, 635–644].

The silicone elastomers used in the carbon dioxide fiber optic sensors are gas permeable membranes capable of separating a bicarbonate solution from the liquid to be analyzed according to the technique of Severinghaus. The silicone elastomers may be polydimethyl siloxanes selected from the group consisting of hydroxy, epoxy, and vinyl terminated polydimethyl siloxanes. Preferably, the silicone elastomer is selected from the group consisting of epoxy and vinyl terminated polydimethyl siloxanes. More preferably, the silicone elastomer is a vinyl terminated polydimethyl siloxane. Particularly preferred silicone elastomers are McGhan NuSil MED-6210 Silicon Intraocular Lens Elastomers A & B (catalyst, Hüls America, Inc. PC072, platinum divinyltetramethylsiloxane complex), Petrazch Clear encapsulants PS 274, McGhan NuSil MED-6233, and Dow Corning SYLGARD 184.

In the pH fiber optic sensors of the present invention, the amount of fluorescent dye present in the fluorescent dye-polymeric matrisx may be varied to optimize the response to pH in the polymeric matrix. The exact amount of fluorescent dye employed is subject to such factors as the type of fluorescent dye and polymer used. Thus, the ratio of components may be varied in order to obtain the result desired in the final method and such variations are within the capabilities of those skilled in the art without the need for undue experimentation. In general, the fluorescent dye is present in the fluorescent dye-polymeric matrix in an amount from about 0.01% to about 1%, preferably in an amount from about 0.01% to about 0.5%, and more preferably in an amount from about 0.05% to about 0.1%, by weight.

In the carbon dioxide fiber optic sensors of the present invention, the amount of fluorescent dye present in the fluorescent dye-polymeric premix may be varied to vary the permeability and solubility of carbon dioxide in the polymeric matrix. The exact amount of fluorescent dye employed is subject to such factors as the type of fluorescent dye and polymer used. Thus, the amount of fluorescent dye may be varied in order to obtain the result desired in the final method and such variations are within the capabilities of those skilled in the art without the need for undue experimentation. In general, the fluorescent dye is present in the fluorescent dye-polymeric premix in an amount from about 0.1% to about 10%, preferably in an amount from about 0.5% to about 5%, and more preferably in an amount from about 1% to about 2%, by weight of the premix.

In the carbon dioxide fiber optic sensor of the present invention, the amount of fluorescent dye-polymeric premix present in the fluorescent dye-polymeric-silicone elastomeric matrix may be varied to vary the permeability and solubility of carbon dioxide in the polymeric matrix. The exact amount of fluorescent dye-polymeric premix employed is subject to such factors as the type of fluorescent dye, polymer, and silicone elastomer used and the permeability and solubility desired to measure carbon dioxide. Thus, the amount of fluorescent dye-polymeric premix may be varied in order to obtain the result desired in the final method and such variations are within the capabilities of those skilled in the art without the need for undue experimentation. In general, the fluorescent dye-polymeric premix is present in the fluorescent dye-polymeric-silicone elastomeric matrix in an amount from about 1% to about 30%, preferably in an amount from about 5% to about 25%, and more preferably in an amount from about 10% to about 20%, by weight.

In the pH fiber optic sensor of the present invention, the amount of fluorescent dye-polymeric matrix present on the sensor may be varied to vary the response to pH. The exact amount of fluorescent dye-polymeric matrix is subject to such factors as the type of the components used and the permeability and solubility desired to measure protons. Thus, the exact quantity of fluorescent dye-polymeric matrix may be varied in order to obtain the result desired in the final method and such variations are within the capabilities of those skilled in the art without the need for undue experimentation. In general, the fluorescent dye-polymeric matrix is present on the pH fiber optic sensor in an amount sufficient to form a hemispherical tip, preferably about $5.1 \times 10^{-4}$ μL.

In the carbon dioxide fiber optic sensor of the present invention, the amount of fluorescent dye-polymeric-silicone elastomeric matrix present on the sensor may be varied to vary the response to carbon dioxide. The exact amount of fluorescent dye-polymeric-silicone elastomeric matrix is subject to such factors as the type of the components used and the permeability and solubility desired to measure carbon dioxide. Thus, the exact quantity of fluorescent dye-polymeric-silicone elastomeric matrix may be varied in order to obtain the result desired in the final method and such variations are within the capabilities of those skilled in the art without the need for undue experimentation. In general, the fluorescent dye-polymeric-silicone elastomeric matrix is present on the carbon dioxide fiber optic sensor in an amount sufficient to form a hemispherical tip, preferably about $5.1 \times 10^{-4}$ μL.

The fluorescent dye-polymeric matrix in the pH sensors and the fluorescent dye-polimeric-silicone elastomeric matrix in the carbon dioxide sensors of the present invention may also contain conventional additives normally employed in polymers providing the additives do not interfere with the optical and chemical properties of the polymeric matrix. Other useful additives include accelerators, catalysts, stabilizers, plasticizers, and the like, which improve or modify the properties of the polymers. Examples of such useful additives include polypropylene adipate, organic tins, alkyl and aryl amines, hindered phenols, and fatty amides.

For stability during storage, it is desirable to store the fiber optic sensors dry. Short hydration times are therefore needed prior to using the sensors. To decrease the hydration time of the carbon dioxide sensor, the fluorescent dye-polymeric-silicone elastomeric matrix may be prepared with a fine dispersion of bicarbonate micelles in siloxane. Preferably, the fine dispersion of micelles in siloxane have a size in the range of about 1 to 10 microns. Polyvinylpyrrolidone may also be added to the bicarbonate to stabilize the micelles.

The present invention extends to methods for making the pH and carbon dioxide fiber optic sensors. In general, pH sensors may be prepared by dispersing the polymeric hydrogel and the fluorescent dye in a suitable solvent to form a solution with heating if necessary. The polymer is then precipitated from solution by addition of an excess of pH 6 buffer. This precipitation ensures a product with a high degree of purity. A quantity of potassium hydroxide may be added to the dye-polymer solution to adjust the pH value. A concentrated solution of the dye-polymer mixture in a solvent such as in acetone, dioxane, tetrahydrofuran, ethanol, and dimethylacetamide may then be applied to the distal tip of a fiber optical fiber. The sensors are then allowed to cure overnight before use. In general, the carbon dioxide sensors may be prepared by dispersing the polymeric hydrogel, the fluorescent dye, and a solution of sodium bicarbonate to form a solution with heating if necessary. The dye-polymer mixture is then added to the silicone elastomer with mixing. The catalyst may be mixed with the composite material before application to the fiber or the fiber may be dipped into a solution of the catalyst before application of the composite material. The composite material is then applied to the distal end of methacrylate optical fiber. The polymer is allowed to cross-link overnight before use. In accordance with the present invention, the fiber optic sensors may be formed by any conventional method such as by extrusion, casting, injection molding, and the like. The sensors may be of any desired shape, size, or configuration.

The present invention is further illustrated by the following examples which are not intended to limit the effective scope of the claims. All parts and percentages in the examples and throughout the specification and claims are by weight of the final composition unless otherwise specified.

EXAMPLES

Materials

SNARF-1-carboxylate (SNARF-1C), SNARF-1-isothiocyanate (SNARF-1C-ITC), and SNARF-1C-dextran conjugate (SNARF-1C-Dex) were obtained from Molecular Probes, Inc. SNARF-1C-ITC and SNARF-1C-Dex were used as received. SNARF-1C was treated with potassium hydroxide (KOH) in deionized water to pH 10 and then lyophilized to remove the water. The potassium salt of the acid was much easier to dissolve.

Polyhydroxyethylmethacrylate (PHEMA) was obtained from Aldrich and purified as follows: A 10% solution of PHEMA in dimethylacetamide was prepared. The polymer was precipitated by adding a tenfold greater volume of pH 7 aqueous buffer. The aqueous fraction was exchanged with fresh buffer and stirred overnight at 60° C. The polymer was then dried at 55° C. to a constant weight. Gel permeation chromatography indicated a molecular weight distribution, Mw/Mn, of 2.6.

Polyvinylpyrrolidone (PVP) Kollidon 90 was obtained from BASF and used as received. Silicone elastomer, McGhan NuSil MED-6210 Silicon Intraocular Lens Elastomers A & B, and catalyst, Hüls America, Inc. PC072, platinum divinyltetramethylsiloxane complex, were used as received. Optical fiber with a methacrylate core was obtained from Mitsubishi and had a 125 μ outer diameter.

Preparation of the Sensor Chemistry

The pH sensors were prepared by one of the following two procedures:
a) A quantity of 5 g of purified PHEMA was dissolved in dimethylacetamide to make a 10% solution. A quantity of 3 mg of SNARF-1C-ITC was added to the PHEMA solution with stirring. The resulting solution was heated to 65° C. for 2 hours. The polymer was precipitated by adding a 10 fold excess of pH 6 buffer.
b) A quantity of 2.5 g of powdered potassium hydroxide was slowly added to 75 ml of a 10% solution of purified PHEMA in dimethylacetamide. The resulting solution was heated for 2 hours at 80°-90° C. The solution was then allowed to cool and filtered to remove undissolved potassium hydroxide.

A quantity of 1 mg of SNARF-C-ITC was added to the filtered solution. The solution was then stirred for 4 hours at 65° C. The polymer was precipitated by the addition of a 10 fold excess of pH 6 buffer.

The polymers prepared above were soluble in acetone, dioxane, tetrahydrofuran, ethanol, and dimethylacetamide. A concentrated solution of the polymer in one of these solvents was prepared and applied to the distal tip of a methacrylate optical fiber, the tip of which had been prepared by cleaving normal to its longitudinal axis with a fresh scalpel blade. The sensors were allowed to dry overnight before use.

The carbon dioxide sensors were prepared by the following procedure:

A solution of 10 mg of SNARF-1C in 1 mL of 100 mM solution of sodium bicarbonate was prepared. To this was added 100 mg of polyvinylpyrrolidone. The vial was heated to 60° C. and shaken until the polyvinylpyrrolidone had dissolved. Equal amounts of the A and B parts of the MED-6210 silicone elastomer were put into the micro container of an Eberbach mixer. The polyvinylpyrrolidone solution was added and the contents were mixed for 1 minute. The uniform, lathery mixture was whitish-blue and was stable for 10 hours without a catalyst.

The composite material was applied to the distal end of methacrylate optical fiber prepared according to the procedure above. The polymer was allowed to crosslink overnight before use.

Apparatus

Emission spectra were recorded on either a ISS Greg-200 spectrofluorometer or a single-fiber spectrofluorometer discussed below. Absorption spectra were recorded on a Perkin-Elmer Lambda 5 spectrophotometer. Lifetime measurements were recorded with the ISS Greg-200 spectrofluorometer using excitation by a Coherent 700 Dye Laser with Rhodamine 6G synchronously pumped with a frequency doubled Coherent Antares mode-locked Nd:YAG laser. The mode-locker was driven by a Marconi Instruments 2022a frequency synthesizer locked in phase to another Marconi Instruments 2022a frequency synthesizer which modulated the photomultiplier tubes on the Greg-200 instrument.

Emission yields were corrected for instrument response and measured using tetraphenylporphyrin in benzene, $\Phi=0.11$ [Seybold, Paul G.; Gouterman, Martin J. Mol. Spectrosc. 1969, 31, 1–13], as a standard. Lifetime measurements were calibrated with scattered light, $\tau=0$. Photobleaching yields were measured by focussing excitation from a Helium-Neon laser, Melles Griot LGR-025, onto a cuvette of SNARF-1C of known concentration. The output from the laser was measured before and after the experiment to ensure constant excitation intensity. A dilute solution of SNARF-1C in 20 mmol sodium bicarbonate at 37° C. was irradiated with an argon ion laser (514.5 nm, 1.7 mW) for 4.25 hours. The loss of SNARF-1C was followed by monitoring the visible absorption spectrum. A 6% loss of dye was observed.

The sensors were characterized on a single fiber spectrofluorometer illustrated in FIG. 1. The excitation system consisted of a Melles Griot Helium-Neon laser, LGR-025, with emission at 543 nm and an IntraAction Model AOM-40 acoustooptic modulator. The optical system consisted of two 100/140 $\mu$ Amphenol optical couplers. The first coupler separated the excitation from the emission. The second coupler split the emission light in two. Half the light was focused onto either a monochromator or a band-pass filter and the other half was focused onto a band-pass filter which served as the reference channel for the single fiber fluorometer. The detection system consisted of two SPCM-100 RCA photon counting modules. A personal computer was used to trigger the acoustooptic modulator and to collect the data.

The pH values were measured with a Corning Ion Analyzer 250 that had been calibrated using two blood pH reference buffers from Instrumentation Laboratory that were accurate to within 0.005 pH units. Carbon dioxide values were measured with a Servomex 404 IR analyzer with 0%–20% range. The analyzer was calibrated with a standardized gas, 10% carbon dioxide and nitrogen. All measurements were made in thermostated cells.

Results

The instrumentation designed for the sensors incorporates a green He-Ne laser, an acousto-optic modulator to chop the excitation, and avalanche photodiodes operating in a photon counting configuration. The laser was used to mimic the excitation from green light emitting diodes (LED). The intensity used, 1–3 $\mu$W, was comparable to the intensity which can be coupled from a green light emitting diode into a fiber. To use a light emitting diode, however, a band-pass filter is required to eliminate the red emission. This would reduce the excitation available to the dye. The avalanche photodiodes have a sensitivity of $1 \times 10^{-18}$ Einstein/count at 600 nm. The dark count is between 100 and 200 counts/s. The photodiodes are linear to 50,000 counts/s. The excitation was chopped at a rate of 0.5 to 1 Hz. The dark signal was collected and subtracted from the sensor emission to eliminate ambient light. The subtraction was effective; the sensors were tested in room light. As the ambient light increases, the signal to noise ratio decreases with a concomitant decrease in precision. Also, the accuracy is not expected to suffer as long as the ambient light and sensor emission together do not exceed 50,000 counts/s, the linear range of the photodiodes.

The emission yields and lifetimes for the two tautomers of SNARF-1C, the SNARF-1C-Dex, and the SNARF PHEMA conjugate were measured and are listed in Table 1. The emission spectra of SNARF-1C were measured as a function of pH with 540 nm excitation and do not differ from the previously published spectra [Whitaker, James E., Haugland, Richard P., and Prendergast, Franklyn G. Anal. Biochem., 1991, 194, 330–44]. In aqueous solution, the base peak has a maximum at 640 nm. The acid peak has a maximum at 590 nm. The isosbestic point is at 605 nm. The emission yields for both the acid and base forms are concentration dependent. At higher concentrations the emission yields decrease. The emission lifetimes are insensitive to concentration. A nonfluorescent aggregate of SNARF-1C probably forms at higher concentrations resulting in a decrease in the emission yield. Broadening of the absorption maxima at higher concentrations is also indicative of aggregation and is seen for SNARF-1C. The lifetime of the acid tautomer of SNARF-1C is shorter than that for the base tautomer. The 800 psec lifetime measured for the acid tautomer is 200 psec longer than was measured previously [Whitaker, James E., Haugland, Richard P., and Prendergast, Franklyn G. Anal.

Biochem., 1991,194, 330-44]. The base tautomer lifetime is comparable. The lifetimes for SNARF-1C-Dex are similar to their free acid counterparts. The emission yields however are much lower. It is improbable that aggregates can form from the SNARF-1C-Dex conjugates so the origin of the reduced emission yields is unclear. The lifetime of the SNARF-PHEMA conjugate is longer than either the dextran conjugate or the free dye. The chromophoric portion of the dye is the same in SNARF-1C-Dex and SNARF-PHEMA. The environment around the dye in both cases is hydrophilic but the PHEMA has a much higher water content [Brannon-Peppas, L. and Peppas, N. A., Biomaterials 11, 635-644 (1990)].

The desired operating life of the pH and carbon dioxide sensors is 72 hours. The ratiometric measurement of the base peak and the isosbestic point eliminates drift due to fluctuations in signal intensity. As the dye degrades due to photobleaching, however, the decrease in emission reaching the photodetector will yield a decrease in the signal to noise ratio. Photobleaching studies were performed on SNARF-1C to ascertain the amount of performance degradation in a 72 hours period. The photobleaching quantum yield was calculated to be $4.5\times10^{-5}$ using an Argon ion laser emitting at 514.5 nm. The amount of dye depletion was calculated using the photobleaching quantum yield and the amount of light absorbed by the dye at the sensor tip. The intensity of light reaching the end of the optical fiber was kept between 1 and 3 $\mu W$ with a duty cycle of 50%. Assuming an absorptivity of the dye at the end of the fiber of 0.124 ($1\times10^{-3}M$), roughly 5% of the dye would be lost to photobleaching in 72 hours. Little degradation in the system performance is expected.

Figure 3:
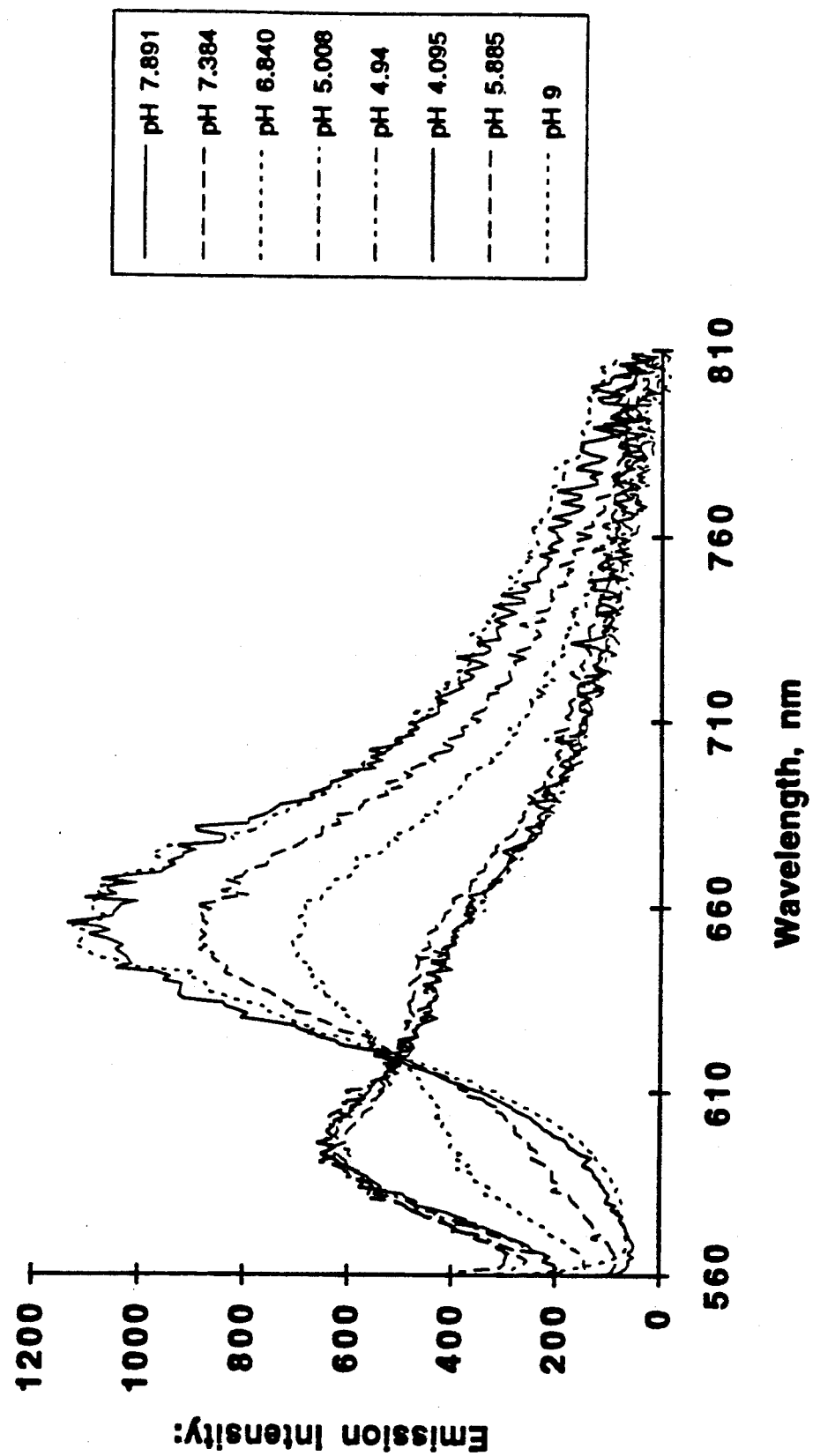
FIG. 3 is the emission spectra of seminaphthorhodaflor-1-carboxylate dextran conjugate (SNARF-1C-Dex) plotted as a function of pH.

SNARF-1C was synthetically modified to incorporate an isothiocyanate so that it could be bound to a polymer support. The structures of SNARF-1C and SNARF-1C-ITC are shown in FIG. 2. The effect of binding the SNARF-1C-ITC to a large molecule was determined by examining the emission spectra of SNARF-Dex as a function of pH. These spectra are shown in FIG. 3 and the spectral data are listed in Table 1. The spectra are shifted to the red compared to SNARF-1C. The isosbestic point is at 620 nm. The $pK_a$ of the conjugated dye is lower than SNARF-1C.

TABLE 1

Photophysical Parameters for the SNARF-1C and Conjugates

| | Conc. M | Φ | τ ns | lambda max, nm | ε $M^{-1}cm^{-1}$ | $pK_a$ |
|---|---|---|---|---|---|---|
| SNARF-1C at 25° C. | | | | | | 7.58 ± 0.04 |
| acid form | | | | | | |
| | 10e-4 | .018 | .78 | 549 | 12650 | |
| | 10e-5 | .12 | .80 | 553 | 19380 | |
| | 10e-6 | .12 | .80 | 551 | 19920 | |
| base form | | | | | | |
| | 10e-4 | .082 | 1.26 | 572 | 27770 | |
| | 10e-5 | .22 | 1.41 | 576 | 37510 | |
| | 10e-6 | .2 | 1.38 | 577 | 38220 | |
| SNARF-1C at 37° C. | | | | | | 7.44 ± 0.05 |
| SNARF-1C-Dex at 37° C. | | | | | | 6.98 ± 0.12 |
| acid form | | .024 | 0.91 | | | |
| base form | | .022 | 1.39 | | | |
| SNARF-PHEMA at 37° C. | | | | | | |
| Untreated | | | | | | 7.89 ± 0.12 |
| acid form | | | | | | |
| base form | | | 2.3 | | | |
| KOH treatment | | | | | | 9.50 ± 0.17 |
| acid form | | | | | | |
| base form | | | 2.5 | | | |

Figure 4:
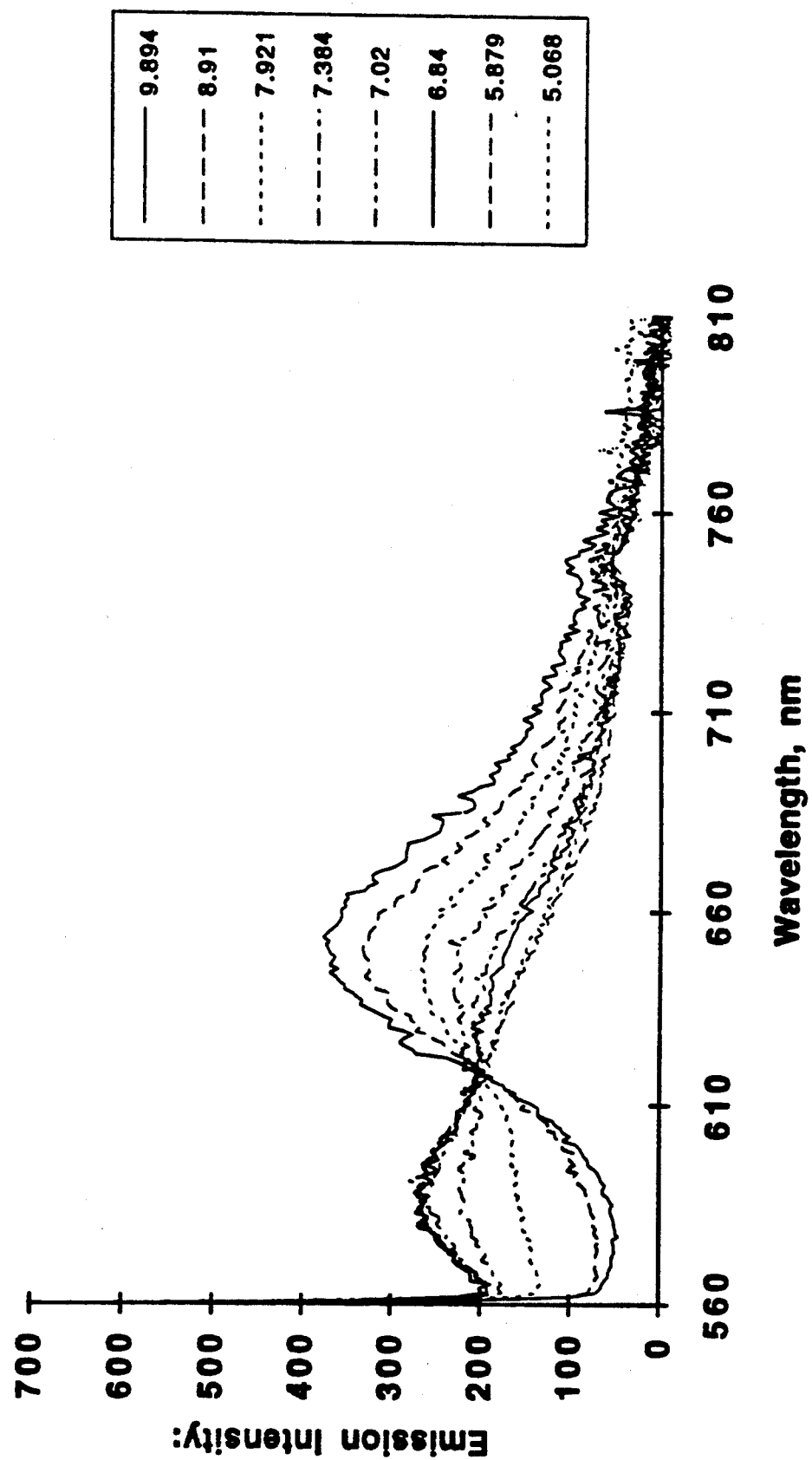
FIG. 4 is the emission spectra of a mixture of seminaphthorhodaflor-1-carboxylate and polyhydroxyethylmethacrylate (SNARF-1C-PHEMA) plotted as a function of pH.

The emission spectra of SNARF-1C-ITC bound to 1M MW polyHEMA as a function of pH are shown in FIG. 4. The spectral data are listed in Table 1. The spectra do not differ significantly from SNARF-1C-Dex. The $pK_a$ is shifted basic relative to SNARF-1C.

The effect of temperature on the parameters describing the pH dye was determined. SNARF-1C was mixed with a series of twelve isotonic buffers ranging from pH=4.0 to 10.0. The emission spectra were measured as a function of pH at 20° C., 25° C., 30° C., 37° C., and 45° C. The spectra did not shift with temperature. The relative emission intensity, B, was defined as the ratio of the emission from the base tautomer at 650 nm to the emission from the isosbestic point. The relative emission, A, was defined as the ratio of the isosbestic point emission to the emission from the acid tautomer at 650 nm. The quantities A and B define the upper and lower asymptotes on the response vs. pH sigmoidal curve. The $pK_a$, A, and B were determined for the series of emission spectra at each temperature by fitting the emission intensity at 650 nm to the theoretical response vs. pH curve using non-linear regression. The results are shown in Table 2.

TABLE 2

Emission Parameters as a Function of Temperature

| Temperature | $pK_a$ | A | B |
|---|---|---|---|
| 20 | 7.79 ± .03 | .721 ± .062 | 5.07 ± .11 |
| 25 | 7.58 ± .01 | .628 ± .061 | 4.22 ± .10 |
| 30 | 7.57 ± .03 | .678 ± .072 | 4.95 ± .12 |
| 37 | 7.44 ± .04 | .702 ± .069 | 4.10 ± .11 |
| 45 | 7.43 ± .06 | .674 ± .127 | 5.48 ± .19 |

The change in $pK_a$ with temperature is best described as a linear decrease in $K_a$ as a function of T:

$$K_a = (9.4\times10^{-10})T - 2.6\times10^{-7}$$

where T is given in degrees Kelvin. The values for A and B are independent of temperature.

pH sensor

The equilibrium between the acid and base tautomers of SNARF-1C provides the basis for determining the pH. In a given sensor, the total concentration of dye remains constant so that:

$$[HA] + [A^-] = C \quad (1)$$

where [HA] and [A$^-$] are the concentrations of the acid and base forms of the dye, respectively. The dye dissociation constant is given by:

$$K_a = [H^+][A^-]/[HA] \quad (2)$$

By combining equations 1 and 2 one obtains an expression for the concentration of the base form of the dye.

$$[A^-] = (C \times K_a)/([H^+] + K_a) \quad (3)$$

The emission from the pH polymer is a function of the concentrations of the acid and base tautomers and their respective emission yields. In FIGS. 3 and 4, it is apparent that the emission spectrum of the acid tautomer extends to the red of the emission maximum for the base tautomer. The emission monitored at the base peak will thus be nonzero at high acidities. From equation 3, the emission intensity from the base tautomer, $I_B$, is given by:

$$I_B = [A^-]Q = \frac{C \times K_a}{[H^+] + K_a} + A \quad (4)$$

where A is the correction for residual emission from the acid tautomer described above and Q incorporates the emission yield and absorptivity of the base tautomer.

The emission of the base tautomer can be normalized by the emission at the isosbestic point. The ratio $I_B/I_I$ is insensitive to changes in signal intensity due to photobleaching, fiber bending, or excitation variations. The emission from the pH sensor can be modeled as:

$$I_N = \frac{C \times K_a}{[H^+] + K_a} + b' \quad (5)$$

where $I_N$ is the normalized emission $I_B/I_I$, and C' and b' are normalized parameters. Rearrangement of Equation 5 yields [H$^+$] as a function of $I_N$ and three parameters:

$$[H^+] = \frac{P_1 \times P_2}{I_N - P_3} - P_2 \quad (6)$$

where $P_1 = C''$, $P_2 = K_a$, and $P_3 = b'$.

Using experimental design analysis techniques [Hunter, William G., Hill, William J., Henson, Thomas L. "Designing experiments for precise estimation of all the constants in a mechanistic model." Can. J. Chem., 1969, 47, 76–80], it was discovered that the optimal number of pH levels needed to calibrate the pH probe is three. One level is at the lower limit of pH range of interest (6.5 pH units), the second near the $pK_a$ of the sensor (7.4 pH units), and the third at the high limit (8.0 pH units). The technique used is related to maximizing the volume of highest probability density region for the parameters and involves the minimization of $$J = \det(M^{-1}) \quad (7)$$

where M is called the parameter information matrix [Opitz, N. and Lübbers, D. W.; Adv. Exp. Med. Biol. 1984, 180, 757–762].

The search for the pH calibration values started by fixing two pH levels and varying a third. A minimum of three pH levels is required since there are three parameters to be estimated. It is assumed that a single measurement is made at each level. When an optimum is found, the pH value that was allowed to vary was then fixed at the level which gave the optimum estimates and another was allowed to vary. This was repeated until all three points had been determined. The results of this procedure were the three pH levels mentioned above. When a fourth measurement was added, the study shows that the best estimate would result if this measurement was made at one of the three optimal pH values that had been already determined. The same is true for the fifth and sixth measurements. Thus, the procedure suggests that only three pH levels are needed to calibrate the probe. This result has been confirmed [Hunter, William G., Hill, William J., and Henson, Thomas L., Can. J. Chem. 1969, 47, 76–80]. More measurements at each level will lead to more precise estimates. It was determined that at least 15 measurements are needed for each pH value before the optimal criterion in Equation 7 flattens out. The procedure above assumes that the preliminary estimate of $pK_a$ is relatively accurate. Otherwise an iterative scheme, similar to the one proposed in Baldini, Francesco; SPIE Vol. 1368 *Chemical, Biochemical, and Environmental Fiber Sensors II*, 1990, 184–190, may be necessary.

Figure 5A:
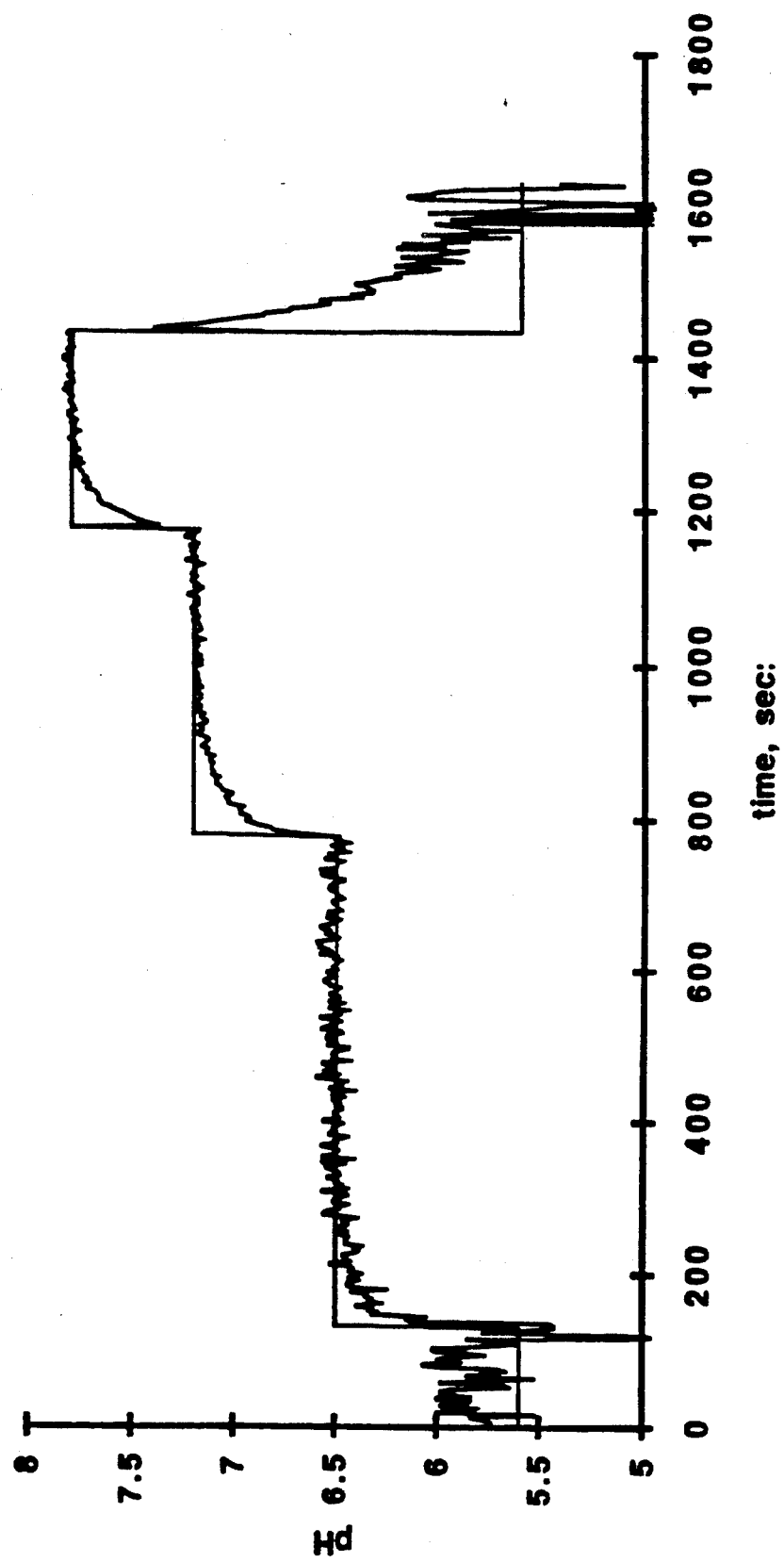
FIG. 5A is a graph illustrating the performance of a pH fiber optic sensor plotted as a function of time in a pH 6.5, 7.2, and 7.8 buffer solution coated on 125$\mu$ optic fibers.

The sensors were prepared by dissolving the pH polymer in acetone and applying the solution to the distal end of 125μ optical fibers. The sensors were ready for testing after 12 hours. The pH response of this sensor was tested in several isotonic buffers. The response of the sensors to the buffers is shown in FIGS. 5a and 5b.

The time for 95% response was calculated and was less than 90 seconds. The hydration time for 95% response was measured and is 60 seconds. The sensors provide an accuracy of less than 10 mpH over the range 6.8 to 7.8. The point to point repeatability was 25 mpH over the same range. The data are summarized in Table 3. The precision is highest for measurements near the $pK_a$ of the dye.

TABLE 3

| Summary of the performance of the pH sensors | | | | |
|---|---|---|---|---|
| | Sensor 1 | | Sensor 2 | |
| pH | Bias | ± 1 SD Precision | Bias | ± 1 SD Precision |
| 6.5 | 0.001 | 0.045 | −0.019 | 0.034 |
| 7.2 | −0.004 | 0.024 | 0.003 | 0.012 |
| 7.8 | −0.01 | 0.015 | 0.002 | 0.013 |
| 95% rt | 108 s | | 36 s | |

The $pK_a$ of SNARF-1C was sensitive to its polymer environment. In dye/polymer films prepared from PHEMA which had been pretreated with potassium hydroxide, the $pK_a$ was at least 1.6 units more basic than films prepared from PHEMA which had no pretreatment. It was difficult to obtain stable measurements at pH 9 and above due to hydrolysis of the dye-polymer bonds. The time for 95% response to pH changes was much longer in the pretreated films than in the normal films. Films prepared in alkaline conditions have a larger degree of cross-linking [Ricka, J., Tanaka, T. Macromolecules, 1985, 18, 83–85]. This was seen in much slower response of these films. The $pK_a$ of the normal films is close to the $pK_a$ of the dye in free solution. We attribute the increase in the $pK_a$ of potassium hydroxide pretreated films to increased degree of cross-linking which brings the dye into greater contact with the polymer backbone. The decrease in solvation available to the dye under these conditions increases the energy of the base tautomer thereby increasing the $pK_a$ of the dye.

Carbon Dioxide Sensor

The principle of operation for the carbon dioxide sensor is analogous to that of a carbon dioxide electrode [Stow, R. W.; Randall, B. F. Am. J. Physiol. 1954, 179, 678]. A pH dye is incorporated into a bicarbonate buffer which is isolated from the liquid by a gas permeable membrane. In practice, micelles of polyvinylpyrrolidone, bicarbonate buffer, and SNARF-1C were dispersed in a silicone matrix. The response of carbon dioxide is linear with the hydrogen ion concentration [Opitz, N.; Lübbers, D. W. Adv. Exp. Med. Biol. 1984, 180, 757–762], and consequently, the pH of the micelles as measured by the SNARF-1C can be directly translated into carbon dioxide concentration. These changes are governed by the following equilibria:

$$CO_2(g) + H_2O \Longleftrightarrow CO_2(l) + \quad (8)$$

$$H_2O \Longleftrightarrow H_2CO_3 \Longleftrightarrow H^+ +$$

$$HCO_3^- \Longleftrightarrow 2H^+ + CO_2^{2-}$$

Figure 6:
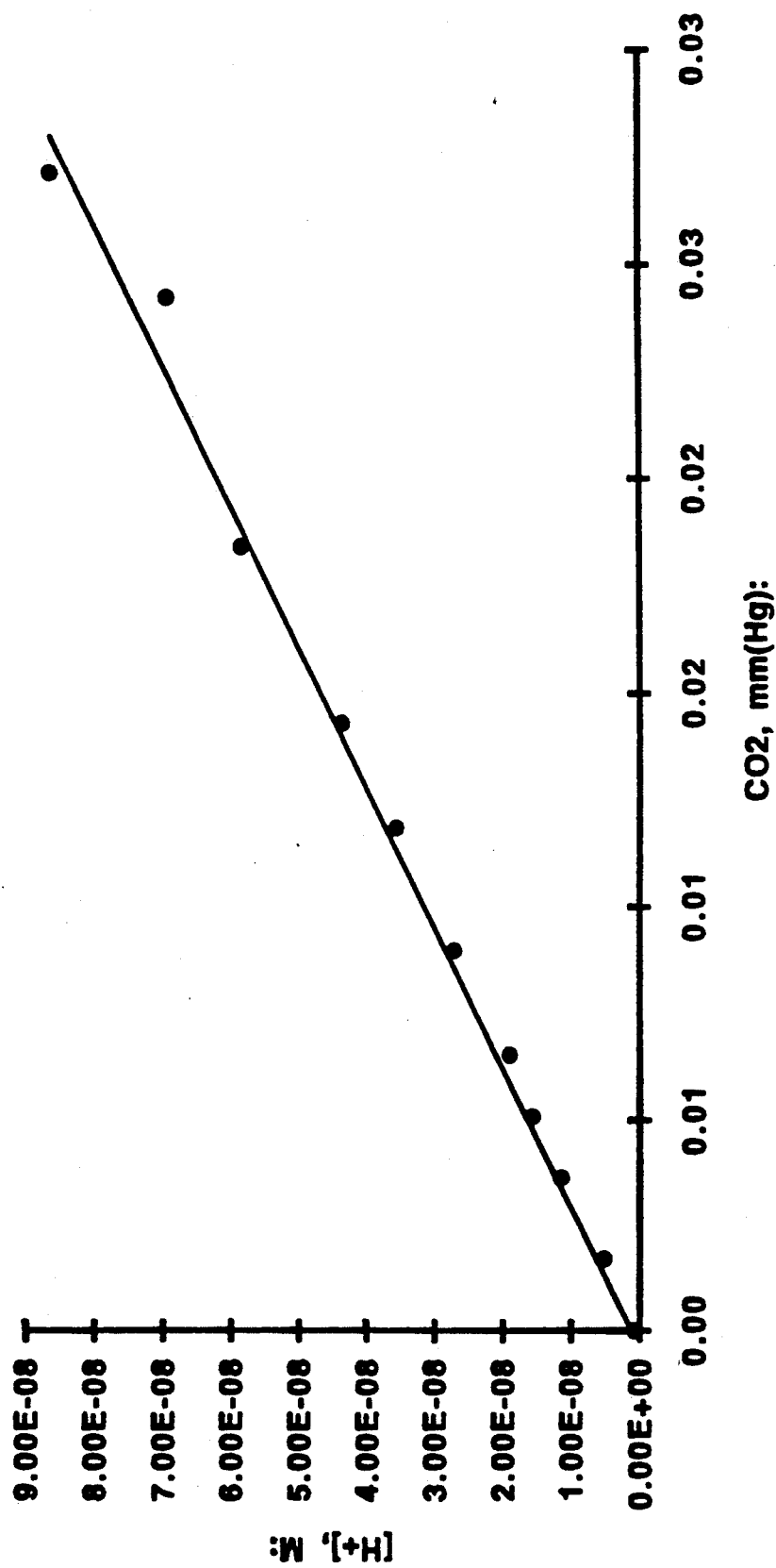
FIG. 6 is a graph illustrating the performance of a pH fiber optic sensor plotted as a function of $PCO_2$ in 20 mmol bicarbonate buffer and 10% by weight polyvinylpyrrolidone.

The dissociation to carbonate ion is negligible. Using values for the solubility of carbon dioxide in water [Lange's Handbook of Chemistry, John A. Dean, Ed., McGraw-Hill Book Company, New York, 1985] of 0.759 ml carbon dioxide @ STP/ml water and 6.35 and 10.33 for the $pK_{a1}$ and $pK_{a2}$ at 25° C., [Peters, Dennis G.; Hayes, John M.; Hieftje, Gary M. A Brief Introduction to Modern Chemical Analysis, W. B. Saunders Company, Philadelphia, 1976] the plot of [H+] vs $PCO_2$ is linear at values of carbon dioxide above 10 mm(Hg). The [H+] was measured using a pH electrode as a function of $PCO_2$ for a solution of 100 mM sodium bicarbonate and 10% polyvinylpyrrolidone in 100 mM sodium bicarbonate. The results are shown in FIG. 6. The plots are linear over the measurement range.

The sensor operation can be adequately described by the Henderson-Hasselbalch model that incorporates only the first dissociation of carbonic acid [Severinghaus, J. W.; Bradley, A. F. "Electrodes for Blood and $pO_2$ and $pCO_2$ Determination" J. Appl Physiol., 1958, 13 515–520]. In bicarbonate buffers, the formation of carbonate need only be considered at high pH values and low temperatures. Consequently, the relationship between carbon dioxide and pH can be described by:

$$[H^+] = \alpha PCO_2 \quad (9)$$

where $\alpha$ incorporates the solubility coefficient of carbon dioxide in buffer, the first acid dissociation constant for carbonic acid, and the concentration of bicarbonate; and $PCO_2$ is the partial pressure of carbon dioxide.

Equation 9 can be combined with Equation 4 that describes the behavior of SNARF-1C to give:

$$I_B = \frac{C \times K_a}{\alpha PCO_2 + K_a} + b \quad (10)$$

By using $I_B/I_I$ one obtains an expression for carbon dioxide as a function of $I_N$ with three parameters:

$$PCO_2 = \frac{P_1 \times P_2}{I_N - P_3} - P_2 \quad (11)$$

where $P_1 = C'$, $P_2 = K_a/\alpha$, and $P_3 = b'$.

The models for the carbon dioxide and pH sensors have essentially the same form. Both models have three unknown parameters that have to be determined under controlled circumstances for measurements of carbon dioxide or pH to be made.

Figure 7:
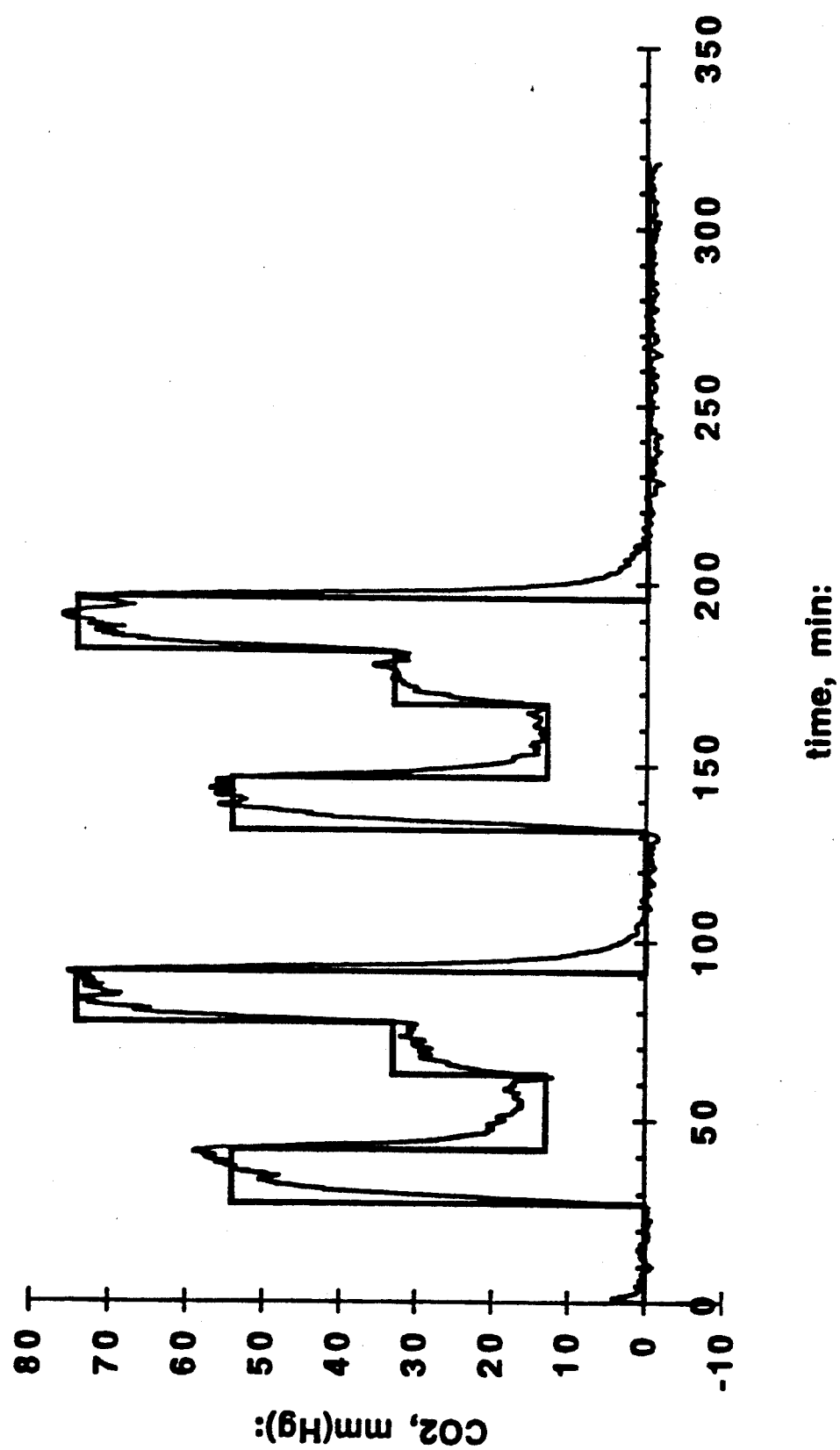
FIG. 7 is a graph illustrating the performance of a carbon dioxide fiber optic sensor plotted as a function of time at different carbon dioxide levels.
Figure 8:
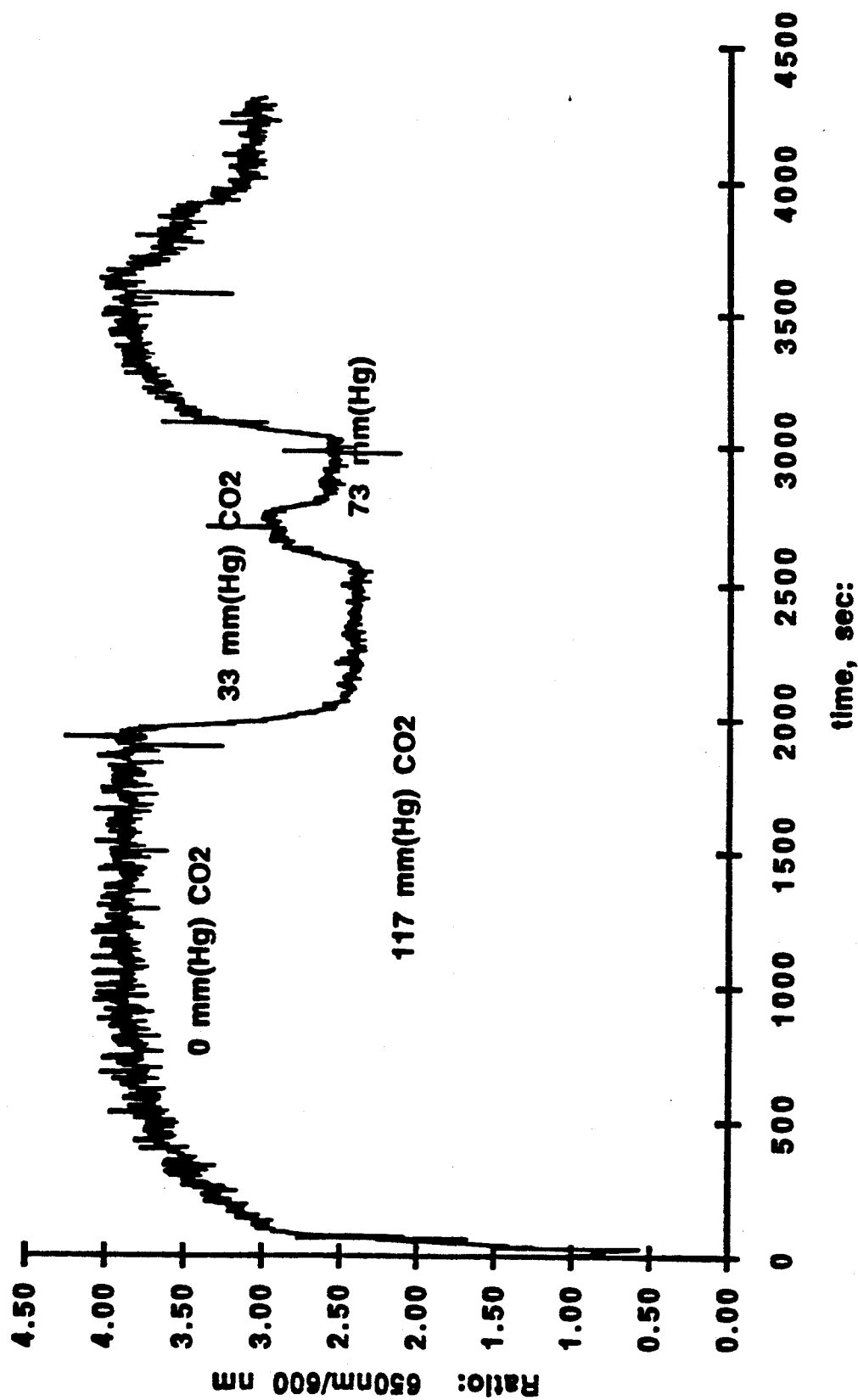
FIG. 8 is the emission spectra of SNARF-1C:polyvinylpyrrolidone:siloxane coated on 125$\mu$ optic fibers plotted as a function of time.

The carbon dioxide polymer was applied to the distal end of 125μ optical fibers. The carbon dioxide response of this sensor was tested in aqueous solution into which gas of several different carbon dioxide concentrations was bubbled. The responses of two of the sensors is shown in FIGS. 7 and 8.

The time for 95% response was calculated and was less than 180 seconds. The hydration time for 95% response was measured and was less than 15 minutes. The sensors provide an accuracy of less than 2 mm(Hg) over the range 10 to 120 mm(Hg). The point to point repeatability was less than 2 mm(Hg) over the same range. The data are summarized in Table 4. The sensors show more drift than was expected for a dye using a self-ratioing scheme.

TABLE 4

Summary of the performance of carbon dioxide sensors

| Sensor 1 | | | Sensor 2 | | |
|---|---|---|---|---|---|
| $CO_2$ mm (Hg) | Bias | Precision ±1 SD | $CO_2$ mm (Hg) | Bias | Precision ±1 SD |
| 0 | −0.13 | 1.37 | 0 | −0.16 | 0.40 |
| 10 | 0.87 | 0.95 | 13 | −1.62 | 1.24 |
| 26 | −0.27 | 0.45 | 33 | −1.81 | 0.58 |
| 33 | 0.14 | 0.51 | 54 | −2.32 | 0.82 |
| 75 | −3.60 | 2.83 | 74 | 2.17 | 1.45 |
| 117 | 0.03 | 3.09 | | | |

While we have represented a number of embodiments of this invention, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

We claim:

1. A fiber optic sensor for analyzing pH which comprises:
   (a) a fluorescence-based fiber optic sensor; and
   (b) a fluorescent dye-polymeric matrix in contact with the sensor, wherein the fluorescent dye is seminaphthorhodaflor-1-isothiocyanate, the polymer is a hydrogel selected from the group consisting of polyhydroxyethylmethacrylate, polyvinylpyrrolidone, cellulose, dextrans, and polysaccharides, and the dye is chemically bonded to the polymer.

2. The fiber optic sensor according to claim 1, wherein the polymer is selected from the group consisting of polyhydroxyethylmethacrylate, polyvinylpyrrolidone, cellulose, and dextrans.

3. The fiber optic sensor according to claim 2, wherein the polymer is selected from the group consisting of polyhydroxyethylmethacrylate and polyvinylpyrrolidone.

4. The fiber optic sensor according to claim 1, wherein the fluorescent dye is present in the fluorescent dye-polymeric matrix in an amount from about 0.01% to about 1%, by weight.

5. The fiber optic sensor according to claim 4, wherein the fluorescent dye is present in the fluorescent dye-polymeric matrix in an amount from about 0.01% to about 0.5%, by weight.

6. The fiber optic sensor according to claim 1, wherein the fluorescent dye-polymeric matrix has a $pK_a$ in the range from about 6.5 to about 10.

7. A fiber optic sensor for analyzing carbon dioxide which comprises:
   (a) a fluorescence-based fiber optic sensor; and
   (b) a fluorescent dye-polymeric-silicone elastomeric matrix in contact with the sensor, wherein the matrix comprises a fluorescent dye-polymeric premixture in a silicone elastomer, and the fluorescent dye is selected from the group consisting of seminaphthorhodaflor-1-carboxylate (SNARF-1C)), seminaphthorhodaflor-1-isothiocyanate (SNARF-1C-ITC), seminaphthorhodaflor-1-dextran conjugate (SNARF-1C-Dex), 10-diethylamino seminaphthorhodaflor-1-carboxylate (SNARF-2C), and seminaphthorhodaflor-1-carboxylate 10-acetate (SNAFL-1C diacetate), the polymer is a hydrogel selected from the group consisting of polyhydroxyethylmethacrylate, polyvinylpyrrolidone, cellulose, dextrans, and polysaccharides, and the silicone elastomer is a polydimethyl siloxane selected from the group consisting of hydroxy, epoxy, and vinyl terminated polydimethyl siloxanes.

8. The fiber optic sensor according to claim 7, wherein the fluorescent dye is selected from the group consisting of seminaphthorhodaflor-1-carboxylate, seminaphthorhodaflor-1-isothiocyanate, and seminaphthorhodaflor-1-dextran conjugate.

9. The fiber optic sensor according to claim 8, wherein the fluorescent dye is seminaphthorhodaflor-1-carboxylate.

10. The fiber optic sensor according to claim 7, wherein the polymer is selected from the group consisting of polyhydroxyethylmethacrylate, polyvinylpyrrolidone, cellulose, and dextrans.

11. The fiber optic sensor according to claim 10, wherein the polymer is selected from the group consisting of polyhydroxyethylmethacrylate and polyvinylpyrrolidone.

12. The fiber optic sensor according to claim 7, wherein the silicone elastomer is selected from the group consisting of epoxy and vinyl terminated polydimethyl siloxanes.

13. The fiber optic sensor according to claim 12, wherein the silicone elastomer is a vinyl terminated polydimethyl siloxane.

14. The fiber optic sensor according to claim 7, wherein the fluorescent dye is present in the fluorescent dye-polymeric premix in an amount from about 0.1% to about 10%, by weight.

15. The fiber optic sensor according to claim 14, wherein the fluorescent dye is present in the fluorescent dye-polymeric premix in an amount from about 0.5% to about 5%, by weight.

16. The fiber optic sensor according to claim 7, wherein the fluorescent dye-polymeric premix is present in the fluorescent dye-polymeric-silicone elastomeric matrix in an amount from about 1% to about 30%, by weight.

17. The fiber optic sensor according to claim 16, wherein the fluorescent dye-polymeric premix is present in the fluorescent dye-polymeric-silicone elastomeric matrix in an amount from about 5% to about 25%, by weight.

18. The fiber optic sensor according to claim 7, wherein the fluorescent dye-polymeric premixture has a $pK_a$ in the range from about 7 to about 9.

19. The fiber optic sensor according to claim 7, wherein the fluorescent dye-polymeric premixture is present in the silicone elastomer as a fine dispersion in the range of about 1 to 10 microns.

* * * * *